(12) United States Patent
Hernandez et al.

(10) Patent No.: US 6,355,931 B1
(45) Date of Patent: Mar. 12, 2002

(54) SYSTEM AND METHOD FOR 100% MOISTURE AND BASIS WEIGHT MEASUREMENT OF MOVING PAPER

(75) Inventors: Jose E. Hernandez, Livermore; Jackson C. Koo, San Ramon, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/386,533

(22) Filed: Aug. 30, 1999

Related U.S. Application Data

(60) Provisional application No. 60/102,859, filed on Oct. 2, 1998, provisional application No. 60/103,863, filed on Oct. 12, 1998, and provisional application No. 60/124,452, filed on Mar. 15, 1999.

(51) Int. Cl.[7] .................................................. D21F 7/06

(52) U.S. Cl. ............................... 250/341.1; 250/339.1; 250/339.11; 250/359

(58) Field of Search ........................ 250/341.1, 339.1, 250/339.11, 359

(56) References Cited

U.S. PATENT DOCUMENTS

| | | |
|---|---|---|
| 4,823,008 A | 4/1989 | Sturm |
| 4,840,706 A | 6/1989 | Campbell |
| 4,965,452 A | 10/1990 | Sturm |
| 5,033,207 A | 7/1991 | Sturm et al. |
| 5,563,809 A | 10/1996 | Williams et al. |
| 5,870,926 A * | 2/1999 | Saito et al. ............ 250/339.11 |

OTHER PUBLICATIONS

CCD–Based Sensor Instrumentation For 100% On–Line Measurements Of Paper Web Properties (Task 3.1), FY97 Progress Report, Jose E. Hernandez et al, Lawrence Livermore National Laboratory, Sep. 17, 1997, pp. 1–10.

CCD Camera–Based Imaging Systems For 100% Web Measurements, Measurement Technology Committee Meeting, Berkeley, CA, May 20, 1997, Jose E. Hernandez.

Improved Infrared Moisture Measuring Techniques, Peter G. Mercer, Systems Development Engineer, Paul Lippke GmbH & Co., KG, 5450 Neuwield 1, West Germany, pp. 93–101.

Dryer Section Energy use Reduced Up To 15% With Computer Control, Pulp & Paper, May 1980, pp. 93–95.

Having Confidence In On–Line Instruments, Steven P. Sturm, Tappi Journal, Oct. 1998, pp. 104–108.

E–mail Correspondence From Jose E. Hernandez to Lloyd E. Dakin, Jr., Jul. 14, 1999, Subject: Re: IL–10265 Claims.

* cited by examiner

*Primary Examiner*—Constantine Hannaher
*Assistant Examiner*—Andrew Israel
(74) *Attorney, Agent, or Firm*—L. E. Carnahan; Alan H. Thompson

(57) ABSTRACT

A system for characterizing a set of properties for a moving substance are disclosed. The system includes: a first near-infrared linear array; a second near-infrared linear array; a first filter transparent to a first absorption wavelength emitted by the moving substance and juxtaposed between the substance and the first array; a second filter blocking the first absorption wavelength emitted by the moving substance and juxtaposed between the substance and the second array; and a computational device for characterizing data from the arrays into information on a property of the substance. The method includes the steps of: filtering out a first absorption wavelength emitted by a substance; monitoring the first absorption wavelength with a first near-infrared linear array; blocking the first wavelength from reaching a second near-infrared linear array; and characterizing data from the arrays into information on a property of the substance.

28 Claims, 5 Drawing Sheets

SYSTEM AND METHOD FOR 100% MOISTURE AND BASIS WEIGHT MEASUREMENT OF MOVING PAPER

REFERENCE TO PROVISIONAL APPLICATIONS TO CLAIM PRIORITY

This application claims priority in three provisional applications, all entitled "A Dual-Band Linescan Camera System for Measuring Water Content on a Paper Web." The first provisional application was filed on Oct. 2, 1998 and was assigned serial number 60/102,859, the second provisional application was filed on Oct. 12, 1998 and was assigned serial number 60/103,863, the third provisional application was filed on Mar. 15, 1999 and was assigned serial number 60/124,452.

STATEMENT OF GOVERNMENT INTEREST

The United States Government has rights in this invention pursuant to Contract No. W-7405-ENG-48 between the United States Department of Energy and the University of California for the operation of Lawrence Livermore Laboratory.

BACKGROUND OF THE INVENTION

1. Field of the Invention

The present invention relates generally to systems and methods for paper moisture and basis weight measurement, and more particularly for continuous, wide coverage measurement of paper moisture, and basis weight using a camera assembly.

2. Discussion of Background Art

Paper manufacture is a very energy and waste-intensive industry. A typical paper machine makes paper that is three-hundred inches wide at speeds of up to five-thousand feet per minute. In order to produce a high quality paper product manufacturers would prefer to monitor as many of the properties of a paper web as possible during manufacture to ensure uniformity and high quality throughout the entire web.

During manufacture there are about a dozen properties that are preferably measured, including moisture, thickness, weight, formation, fiber orientation, color, and printability. In an attempt to meet this need, some current on-line paper web measurement systems use a slow-moving scanning platform containing a suite of sensors for measuring many of these properties, including moisture. Moisture is a critical parameter for paper. For instance, since paper is very hydroscopic and too much moisture affects printability, manufactures tend to take a conservative approach and over-dry their paper products, greatly increasing energy costs.

Methods for making moisture measurements based on near-infrared absorption techniques where originally developed in the sixties, e.g., U.S. Pat. No. 3,405,268. Other patents further refined these method by using specific wavelength combinations and mathematical formulations, e.g. U.S. Pat. Nos. 3,551,678, 3,793,524, 3,851,175, 4,052,615, and 4,823,008.

Current practices for online paper measurement of moisture and cellulose content (which is proportional to basis weight) via absorption techniques, incorporate several lead sulfide sensors for measuring wavelengths between 1.8 $\mu$m and to 2.2 $\mu$m. These sensors are mounted on a scanning platform in close proximity to the paper web, and take point measurements. Point measurements are those which only look at one "point" of about an inch square at any one time. This small sensing area, along with the fact that it takes about a minute or more for the scanning platform to move across the width of a typical moving paper web, can result in the production of thousands of feet of paper before a point sensor can cross the full width of the web even once. In such point measurement based systems, typically less than two percent of a total paper web area is actually measured.

In another approach, Charged Couple Device (CCD) linescan camera technology has been used on paper webs for inspection of visible defect flaws and non-uniformity detectable in a visible range, e.g. U.S. Pat. Nos. 4,950,911 and 5,563,809. However, CCD sensor technology, which is based on Silicon, is not capable of detecting those wavelengths in the near-infrared range needed for accurately measuring paper moisture or cellulose content.

If manufacturers had a method for conducting measurements for moisture and cellulose content over one hundred percent of a paper web, paper-drying time could be substantially reduced, resulting in significant energy savings, and improved paper quality.

In response to the concerns discussed above, what is needed is a system and method for 100% paper moisture and cellulose measurement that overcomes the problems of the prior art.

SUMMARY OF THE INVENTION

The present invention is a system and method for 100% measurement of moisture and basis weight on moving paper. Within the system of the present invention, a camera assembly monitors a water absorption wavelength radiated by a substance, such as a paper web, through a first array of photo detectors. The camera assembly monitors a cellulose absorption wavelength radiated by the substance through a second array of photo detectors. The camera assembly monitors a reference wavelength radiated by the substance through a third array of photo detectors. A single optical axis system is used to image the web from a distance and provide the same field of view to each array in the camera assembly. Optical filters, which could include dichroic mirrors or a prism, are used to filter the specific wavelengths to be measured with each of the three arrays. The filters could also be coated directly on the array photo detectors. A computational device or lookup table is used to calculate the moisture content and basis weight of the substance from the water absorption, cellulose absorption, and reference wavelength data received from the camera assembly. Supporting electronics interface signals from the three arrays with the computational device or lookup table. In other aspects of the invention, the first array has a band-pass filter in its optical path transparent to a water absorption wavelength such as 1.45 $\mu$m or 1.94 $\mu$m wavelength; the second array has a band-pass filter in its optical path transparent to a cellulose absorption wavelength such as 1.57 $\mu$m or 2.1 $\mu$m; the third array has a band-pass filter in its optical path transparent to other wavelengths in the near-infrared range which do not include water or cellulose absorption wavelengths, such as 1.3 $\mu$m, or 1.8 $\mu$m.

In other aspects of the invention the first, second, and third linear arrays consist of Indium Gallium Arsenide (InGaAs) linear arrays. These arrays consist of a plurality of photodiodes, sensitive to the near-infrared spectrum. Unlike CCD arrays, InGaAs arrays are sensitive to wavelength between 0.9 $\mu$m and 2.2 $\mu$m. Therefore, these arrays are very suitable for measuring all the wavelength of interest for this application. Furthermore, the array nature of this sensor technology makes it practical to build a high resolution linescan camera system with the use of optics and supporting electronics for 100% inspection of high-speed web processes such as paper.

In other aspects of the invention a light source, which radiates energy within at least an infrared spectral band, is used to illuminate a paper web. The current invention can be used in a transmission mode where the light source is on one side of the web and the camera assembly is on an opposite side, or in a reflection mode where the light source is on a same side of the web as the camera assembly.

In other aspects of the invention, depending on a width of the web, the size of the arrays, a desired resolution of measurement, a distance between the camera assembly and the web, and a field of view of the camera assembly, several camera assemblies might be needed to monitor a full width of the paper web.

The system and method of the present invention are particularly advantageous over the prior art because they permit a full width paper web to be continuously monitored for moisture and basis weight during manufacture. Such monitoring enables faster detection of moisture and basis weight irregularities so that manufacturers can correct problems before miles of off-quality paper are produced. Such monitoring also helps reduce energy costs and waste because the paper web would not be over-dried as now often happens. Integrating the present invention with existing paper web visible defect inspection systems is straightforward, since the same light source and camera enclosures can be shared between the two systems. It might also be practical in some cases to integrate the present invention with other array sensors such as CCD arrays through a single optical axis to measure other properties of the web in parallel with those described here.

These and other aspects of the invention will be recognized by those skilled in the art upon review of the detailed description, drawings, and claims set forth below.

DETAILED DESCRIPTION OF THE PREFERRED EMBODIMENT

Figure 1:
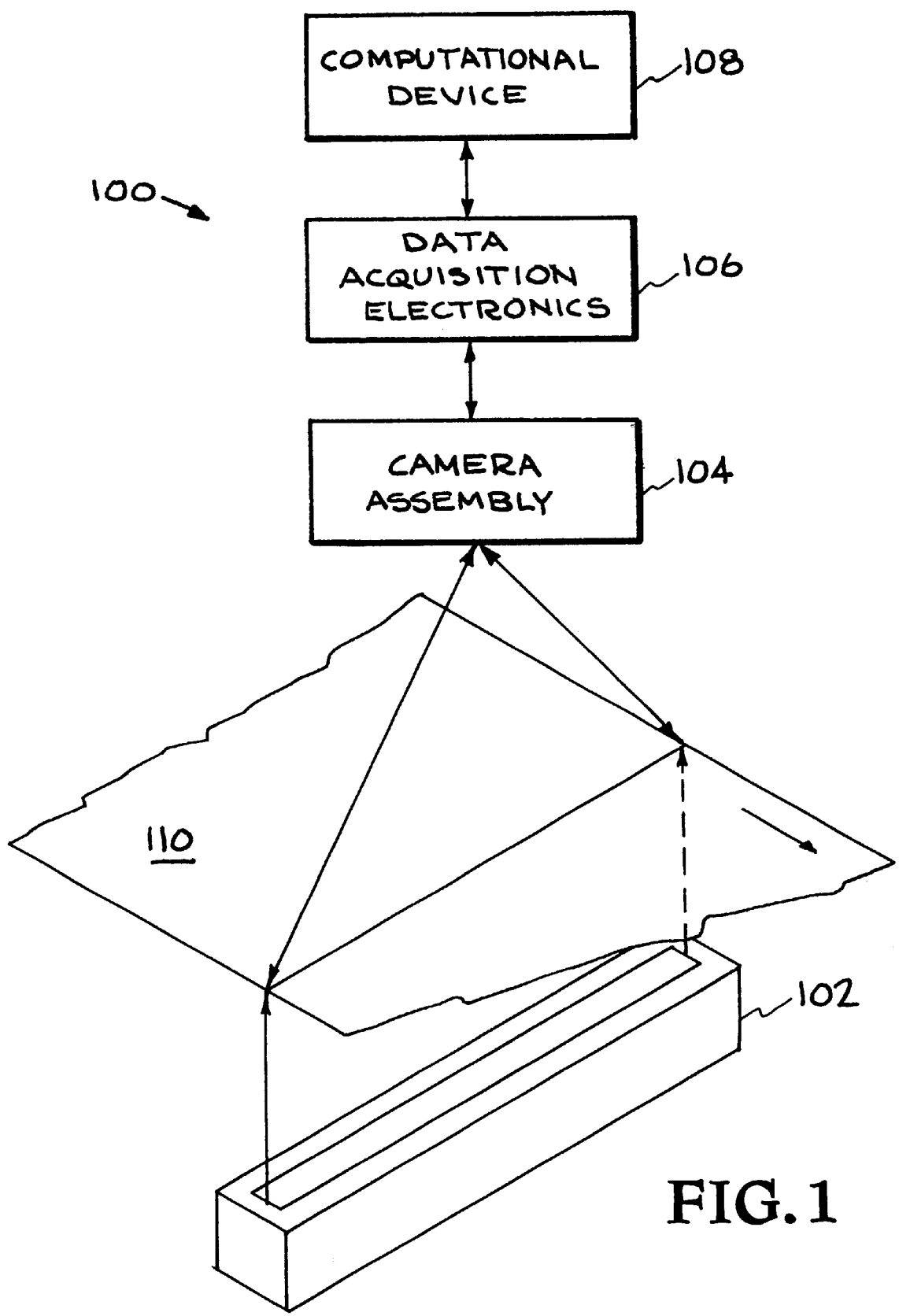
FIG. 1 is a block diagram of a system for moisture and basis weight measurement according to the present invention.

FIG. 1 is a block diagram of a system 100 for moisture and basis weight measurement according to the present invention. The system 100 includes a light source 102, a linescan camera assembly 104, data acquisition electronics 106, and a computational device 108. The system 100 can measure moisture content and basis weight of paper produced by a paper manufacturing machine (not shown) at either a dry end of the machine, or further upstream in the process toward a wet end.

The light source 102 illuminates a paper web 110. Paper web is an industry term for a moving stream of paper, and while the present invention is discussed with respect to the paper web 110, those skilled in the art will know that the system 100 can also measure moisture in other substances such as textiles, sand, salts, aluminum oxide, gypsum, wood chips, fertilizer, plastics, and saw dust for wood products. The light source 102 illuminates an under side of the paper web 110; however, those skilled in the art will know that illumination could also come from a top or at various angles to the paper web 110. The light source 102 radiates energy within the infrared spectral band.

The linescan camera assembly 104 has a set of optics and sensor arrays for acquiring data on various wavelengths of interest re-radiated from the paper web 110 in response to energy absorbed from the light source 102. The wavelengths monitored are chosen so that moisture content and basis weight can subsequently be calculated. Linescan cameras are ideally suited for high speed paper web imaging applications due to their fast scanning rates and compact size. Details on the linescan camera assembly 104 are provided below with reference to FIGS. 2 and 3.

The data acquisition electronics 106 includes electronics for interfacing the camera assembly 104 to the computational device 108. The data acquisition electronics 106 include: a web speed encoder for synchronizing data acquisition with a speed of the paper web; supporting electronics for routing acquired data over cables; and a high speed data capturing system to transfer the data, in either analog or digital form, to the computational device 108.

The computational device 108 incorporates either a computational algorithm for calculating, or a lookup table for mapping the data acquired on the various wavelengths to moisture and basis weight values across the entire paper web. Standard computational algorithms and/or lookup tables are used.

Figure 2:
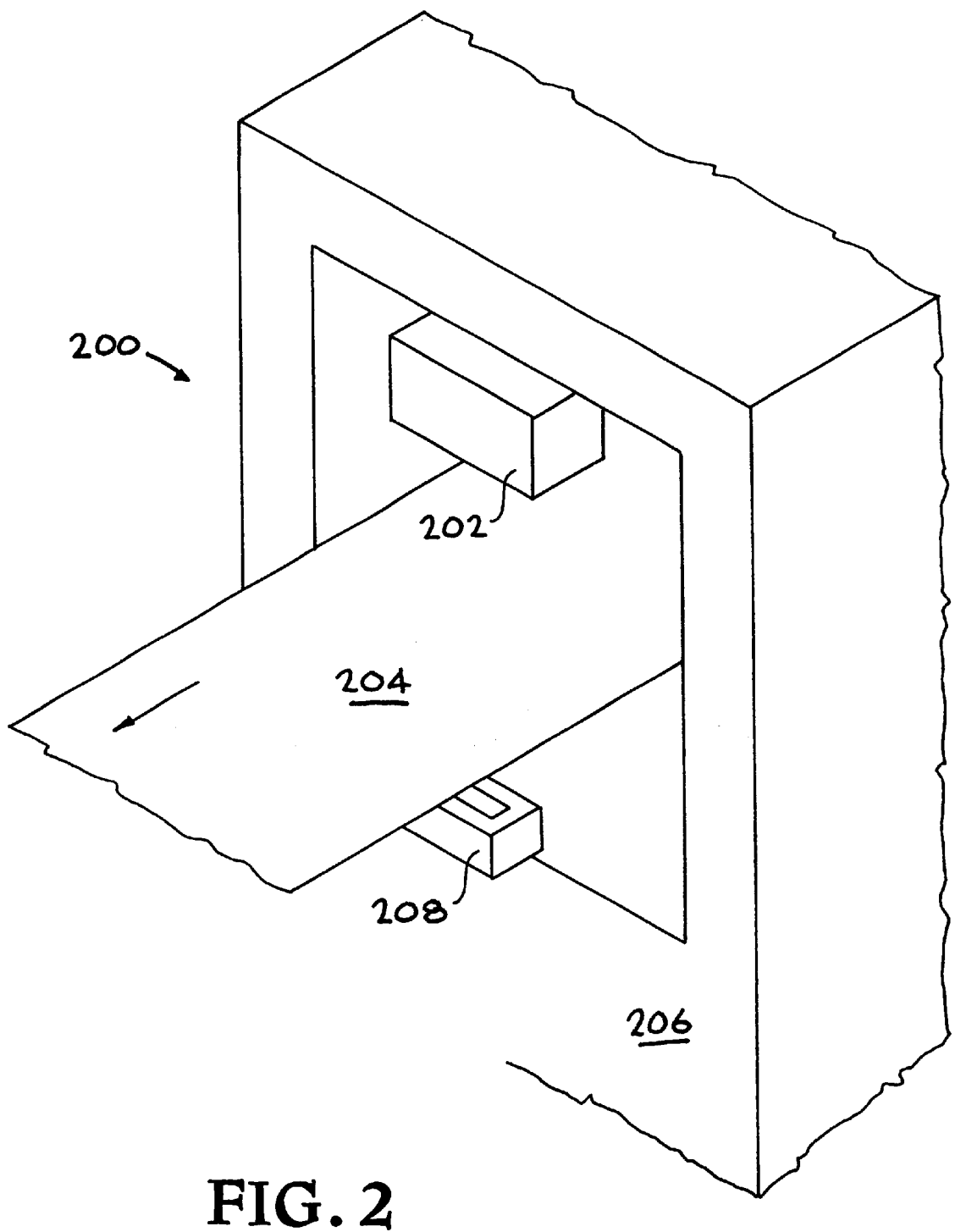
FIG. 2 is a pictorial diagram of a first embodiment of a camera assembly within the system.

FIG. 2 is a pictorial diagram of a first embodiment 200 of the camera assembly 104 within the system 100. The first camera assembly 202 is positioned above a paper web 204 moving within a paper manufacturing machine 206. An below-red light source 208 is positioned underneath the web 204 in this embodiment.

The first camera assembly 202 includes two near-infrared Indium Gallium Arsenide (InGaAs) linescan cameras, such as those manufactured by Sensors Unlimited located in Princeton, N.J. The first camera assembly 202 can be mounted directly on the paper machine and continuously monitor moisture content or basis weight of the paper web during production. Wider paper webs may require additional camera assemblies.

Figure 3:
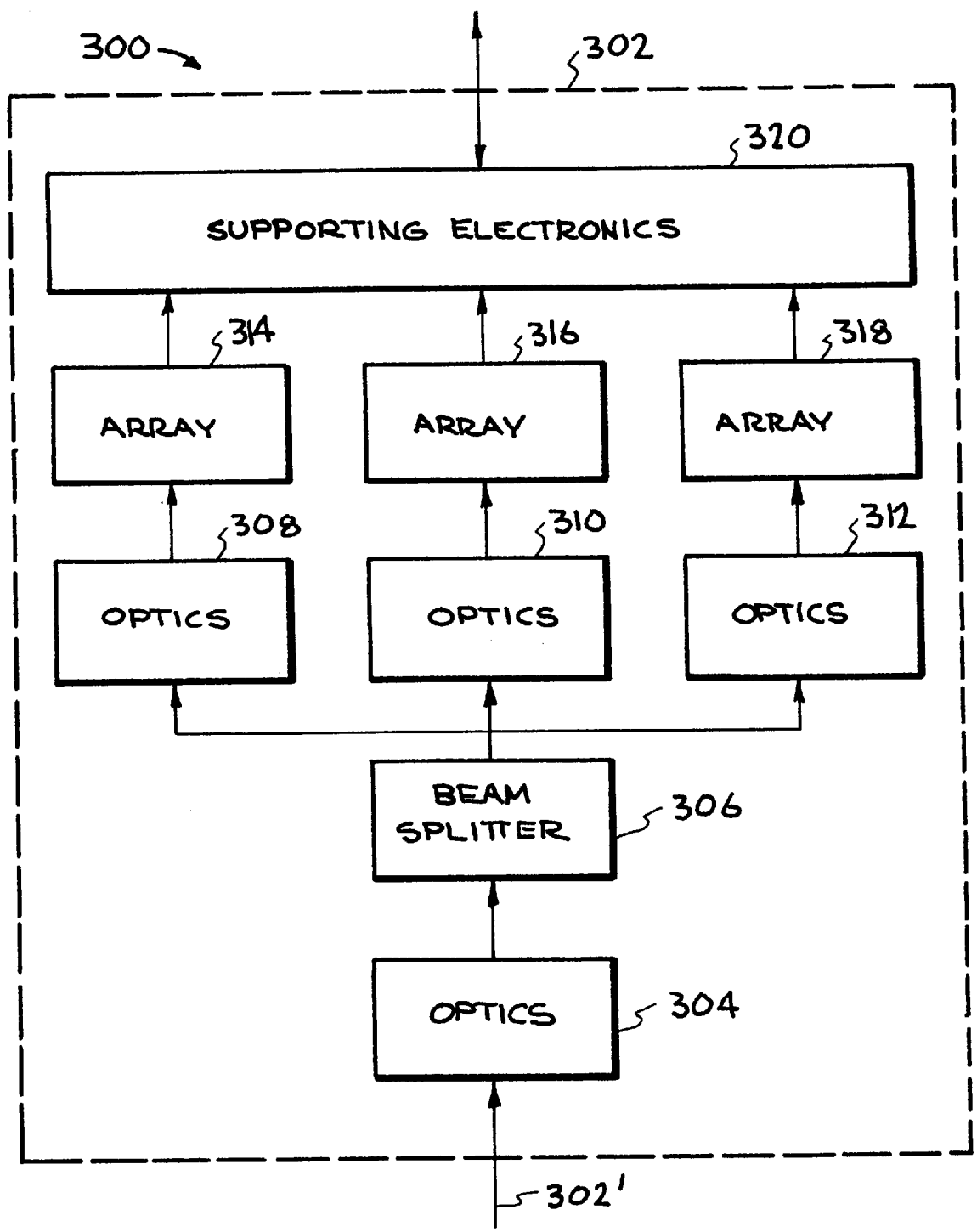
FIG. 3 is a block diagram of a second embodiment of the camera assembly within the system.

FIG. 3 is a block diagram 300 of a second embodiment 302 of the camera assembly 104 within the system 100. The second camera assembly 302 receives the near-infrared energy radiated from the paper web 110 from a single optical axis $302^1$. The radiated energy then passes through a first set of optics 304 which focus and control aperture of the second camera assembly 302. A beam splitter 306 divides the radiated energy three ways. The beam splitter 306 can include a prism and/or dichroic mirrors. A second set of optics 308, 310, and 312 focus radiated energy from the beam splitter 306 to a set of near-infrared InGaAs linear arrays 314, 316, and 318.

Three linear arrays 314, 316, and 318 enable continuous real-time monitoring of three sets of near-infrared wavelengths. By monitoring three wavelengths, both moisture content and cellulose measurements can be made. Those skilled in the art however will recognize that the second camera assembly 302 can also function with only two linear arrays 314 and 316 should only one paper web measurement be required. Since the arrays 314, 316, and 318 are configured about the single optical axis 302, each array is at a same distance from and has a same field of view of the paper web, enabling accurate measurements.

The second camera assembly 302 also includes a set of filters (not shown) placed somewhere from the first set of optics 304 to the linear arrays 314, 316, and 318. For instance, the filters could either be incorporated into the beam splitter 306, into the second set of optics 308, 310, and 312, or directly coated onto the linear arrays 314, 316, and 318. The set of filters are selected so that the linear arrays 314, 316, and 318 can most effectively monitor selected near-infrared wavelengths radiated from the paper web 110. Possible filter selections and combinations will be suggested below with respect to FIGS. 4, 5, and 6.

Supporting electronics 320 collect and interface output signals from the linear arrays 314, 316, and 318 with the computational device 108. The supporting electronics 320 can include a multiplexer for each array, digitizers for digitizing the data of each array, amplifiers, and other signal conditioning electronics.

Figure 4:
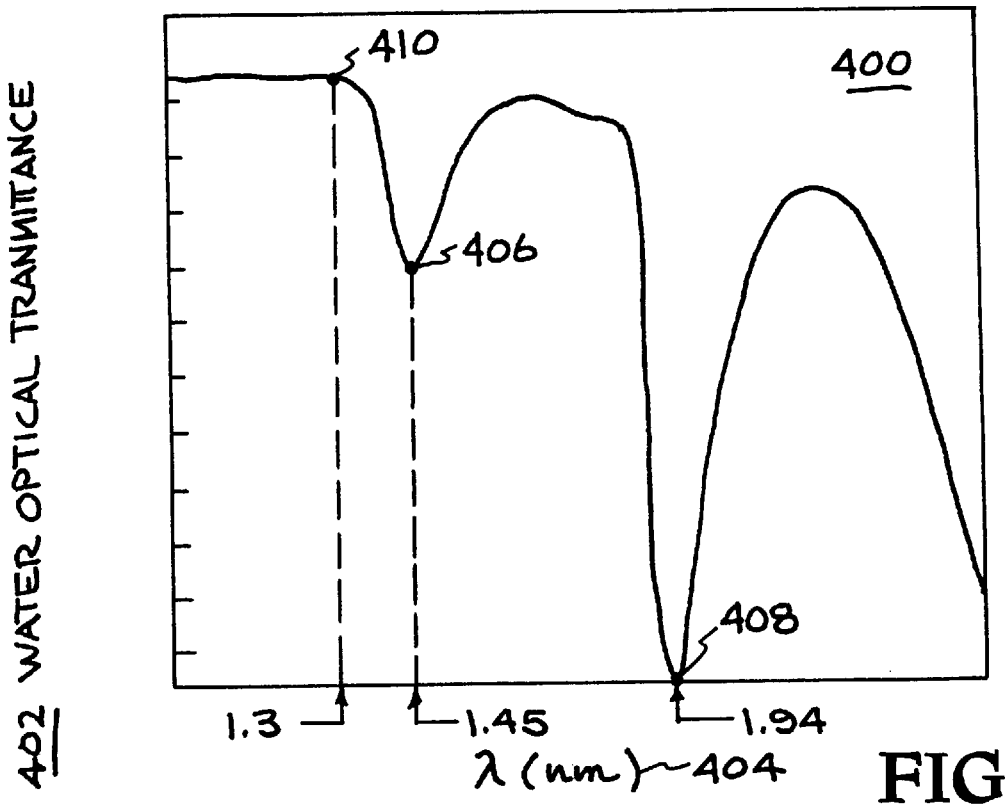
FIG. 4 is an exemplary graph of optical transmittance verses optical wavelength for water.

FIG. 4 is an exemplary graph 400 of optical transmittance 402 verses optical wavelength 404 for water within the paper web 110. As shown, optical transmittance 402 for water varies with the wavelength 404 and includes a first water absorption wavelength 406 at 1.45 $\mu$m and a second water absorption wavelength 408 at 1.94 $\mu$m. The camera assembly 104 can be designed to monitor either the first absorption wavelength 406 the second absorption wavelength 408 or both. "Standard" InGaAs near-infrared linear arrays can monitor the 1.45 $\mu$m wavelength, while "Stressed" InGaAs near-infrared linear arrays can monitor the 1.94 $\mu$m wavelength. Since there is very little water absorption around a wavelength of 1.3 $\mu$m 410, that wavelength 410 is suitable for providing a reference measurement with which to compare the absorption wavelengths 406 and 408 and thus enable moisture content to be determined.

The camera assembly 104 can monitor either one or both of the water absorption wavelengths 406 and 408. The camera assembly 104 also monitors either one or several predetermined reference wavelengths, such as 1.3 $\mu$m 410 and/or 1.8 $\mu$m. The predetermined reference wavelength need only be outside of the water absorption band regions of the paper web 110.

In a preferred embodiment of the present invention, the camera assembly 104 includes standard InGaAs near-infrared linear arrays and monitors the 1.45 $\mu$m water absorption wavelength, and a predetermined reference wavelength located in a range from 1.1 $\mu$m to 1.35 $\mu$m. The standard InGaAs near-infrared linear arrays have better quantum efficiency and dark current characteristics than stressed InGaAs near-infrared linear arrays at these wavelengths. Selecting the 1.45 $\mu$m water absorption wavelength also permits measurement of higher moisture levels than is possible if the 1.94 $\mu$m water absorption wavelength was monitored.

Figure 5:
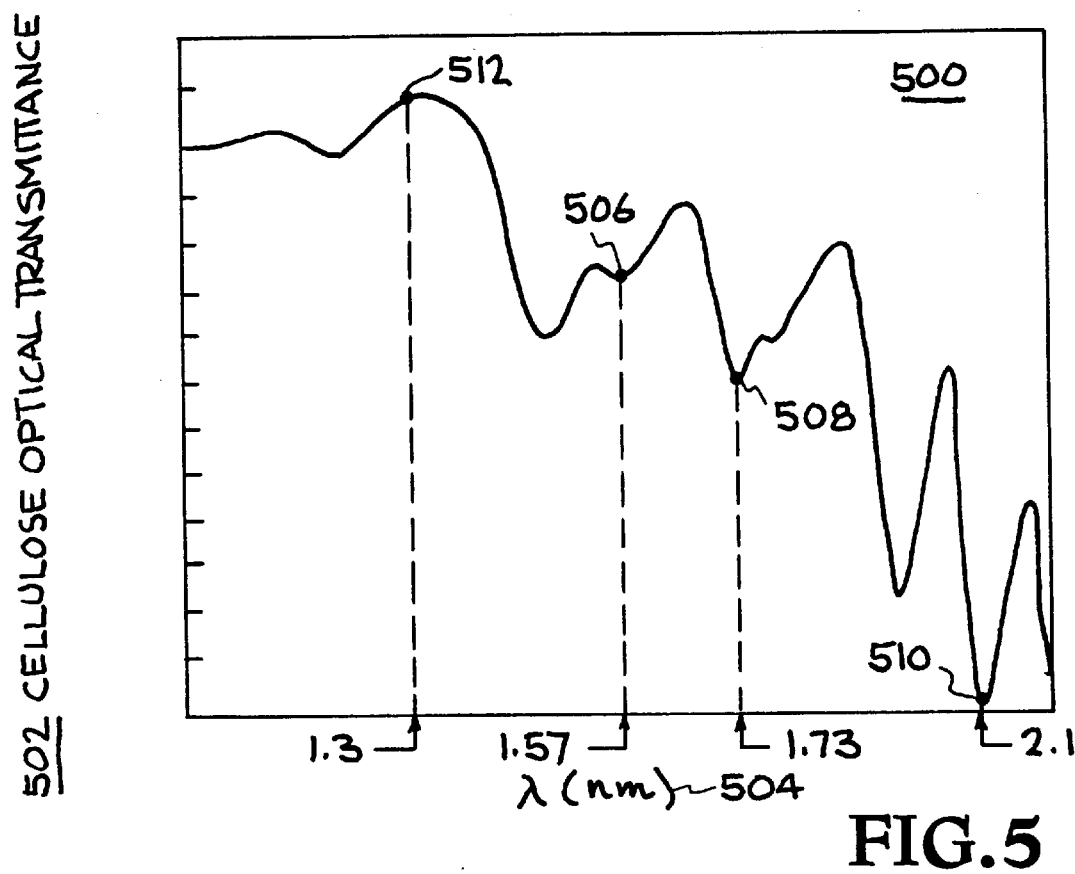
FIG. 5 is an exemplary graph of optical transmittance verses optical wavelength for cellulose.

FIG. 5 is an exemplary graph 500 of optical transmittance 502 verses optical wavelength 504 for cellulose within the paper web 110. As shown, optical transmittance 502 for cellulose varies with the wavelength 504 and includes a first cellulose absorption wavelength 506 at 1.57 $\mu$m, a second cellulose absorption wavelength 508 at 1.73 $\mu$m, and a third cellulose absorption wavelength 510 at 2.1 $\mu$m. The third cellulose absorption wavelength 510 is strongest. Any of the absorption wavelengths 506, 508, 510 can be used with the current invention. "Standard" InGaAs near-infrared linear arrays can monitor the 1.57 $\mu$m wavelength, while "Stressed" InGaAs near-infrared linear arrays can monitor the 2.1 $\mu$m wavelength. Since there is very little cellulose absorption around a wavelength of 1.3 $\mu$m 512, that wavelength 512 is suitable for providing a reference measurement with which to compare the absorption wavelengths 506, 508, 510 and thus enable basis weight to be determined. As an aside, while the graph 500 also shows strong absorption bands at 1.45 $\mu$m and 1.93 $\mu$m, these are probably due to cellulose's hydrophilic properties.

The camera assembly 104 monitors either one or several of the cellulose absorption wavelengths 506, 508 or 510, and either one or several predetermined reference wavelengths, such as 1.3 $\mu$m 512. The predetermined reference wavelengths need only be outside of the cellulose absorption band regions of the paper web 110.

In a preferred embodiment of the present invention, the camera assembly 104 includes standard InGaAs near-infrared linear arrays and monitors the 1.57 $\mu$m cellulose absorption wavelength. The standard InGaAs near-infrared linear arrays have better quantum efficiency and dark current characteristics at 1.57 $\mu$m than stressed InGaAs near-infrared linear arrays do at 2.1 $\mu$m.

Figure 6:
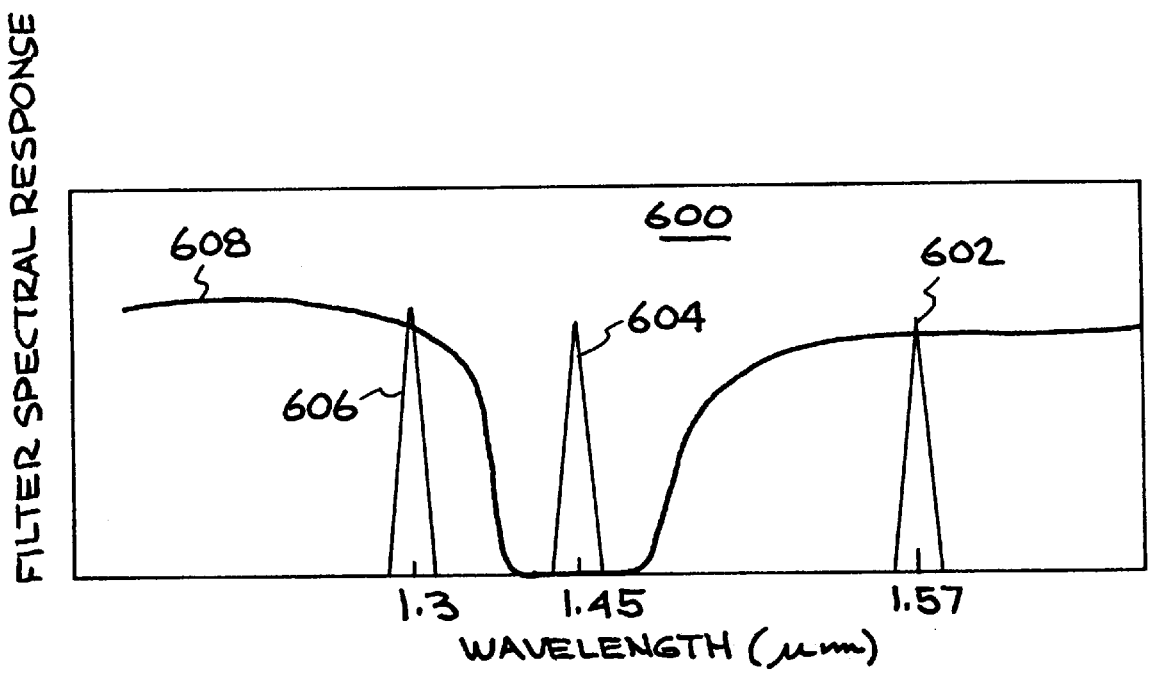
FIG. 6 is a graph illustrating several possible optical filtering configurations for moisture and basis weight measurement.

FIG. 6 is a graph 600 illustrating several possible optical filtering configurations for moisture and basis weight measurement. The graph 600 depicts filter spectral response verses wavelength for various filtering configurations. For instance, a first narrow-band filter 602 for monitoring a cellulose absorption wavelength can be centered about 1.57 $\mu$m. A second narrow-band filter 604 for monitoring a water absorption wavelength can be centered about 1.45 $\mu$m. A third narrow-band filter 606 for monitoring a reference wavelength can be centered about 1.3 $\mu$m. A fourth filter 608 can be a dichroic mirror for providing reference wavelengths for water absorption measurements. A fifth filter (not shown) can be a specialized prism for selectively separating various water, cellulose, and reference wavelengths over by a predetermined number of arc degrees. Using the prism, the arrays would need to be located at specific positions about the prism. In light of the teachings in this invention, those skilled in the art will know that additional filtering arrangements are possible.

While the present invention has been described with reference to a preferred embodiment, those skilled in the art will recognize that various modifications may be made. Variations upon and modifications to the preferred embodiment are provided by the present invention, which is limited only by the following claims.

What is claimed is:

1. A system for characterizing a set of properties for a moving substance comprising:
    a first near-infrared linear array;
    a second near-infrared linear array;
    a first filter transparent to a first absorption wavelength emitted by the moving substance and juxtaposed between the substance and the first array;
    the first absorption wavelength being selected from the group consisting of a water absorption wavelength of 1.45 $\mu$m, and a cellulose absorption wavelength at one of 1.57 $\mu$m, 1.73 $\mu$m, and 2.1 $\mu$m;
    a second filter blocking the first absorption wavelength emitted by the moving substance and juxtaposed between the substance and the second array; and a computational device for characterizing data from the arrays into information on a property of the substance.

2. The system of claim 1, further comprising:
a third near-infrared linear array; and
a third filter transparent to a second absorption wavelength emitted by the moving substance and juxtaposed between the substance and the third array;
wherein,
the second filter blocks the first and second absorption wavelengths.

3. The system of claim 2, wherein:
the first absorption wavelength is a water absorption wavelength; and
the second absorption wavelength is a cellulose absorption wavelength.

4. The system of claim 1 wherein the arrays are InGaAs arrays.

5. The system of claim 1 further comprising:
a beam splitter juxtaposed between the substance and the arrays.

6. The system of claim 1 further comprising:
a dichroic mirror juxtaposed between the substance and the arrays.

7. The system of claim 1 further comprising:
a prism juxtaposed between the substance and the arrays.

8. The system of claim 1 wherein the first absorption wavelength is a water absorption wavelength of 1.94 $\mu$m.

9. The system of claim 8, wherein the water absorption wavelength of 1.45 $\mu$m, the water absorption wavelength of 1.94 $\mu$m, or both can be monitored by one of the near-infrared linear arrays.

10. The system of claim 1, wherein any one or all of the cellulose absorption wavelengths 1.57 $\mu$m, 1.73 $\mu$m, and 2.1 $\mu$m can be monitored by one of the near-infrared linear arrays.

11. The system of claim 1, wherein the near-infrared linear arrays comprise standard InGaAs near-infrared linear arrays and monitors the 1.45 $\mu$m water absorption wavelength, and a predetermined reference wavelength located in a range from 1.1 $\mu$m to 1.35 $\mu$m.

12. The system of claim 1, wherein the near-infrared linear arrays comprise standard InGaAs near-infrared linear arrays and monitors the 1.57 $\mu$m cellulose absorption wavelength.

13. A method for characterizing a set of properties for a moving substance, comprising the steps of:
filtering out a first absorption wavelength emitted by a substance;
the first absorption wavelength being selected from the group consisting of a water absorption wavelength of 1.45 $\mu$m, and a cellulose absorption wavelength at one of 1.57 $\mu$m, 1.73 $\mu$m, and 2.1 $\mu$m;
monitoring the first absorption wavelength with a first near-infrared linear array;
blocking the first wavelength from reaching a second near-infrared linear array; and
characterizing data from the arrays into information on a property of the substance.

14. The method of claim 13 wherein the filtering step includes the step of:
filtering out a water absorption wavelength.

15. The method of claim 13 wherein the filtering step includes the step of:
filtering out a cellulose absorption wavelength.

16. The method of claim 13 further comprising the steps of:
filtering out a second absorption wavelength emitted by the substance;
monitoring the second absorption wavelength with a third near-infrared linear array; and
blocking the first and second wavelength from reaching the second near-infrared linear array.

17. The method of claim 16 wherein:
the first absorption wavelength is a water absorption wavelength; and
the second absorption wavelength is a cellulose absorption wavelength.

18. The method of claim 13 further comprising the step of:
routing emissions from the substance to the arrays with a beam-splitter.

19. The method of claim 13 further comprising the step of:
routing emissions from the substance to the arrays with a dichroic mirror.

20. The method of claim 13 further comprising the step of:
routing emissions from the substance to the arrays with a prism.

21. A system for characterizing a set of properties for a moving substance, comprising:
means for filtering out a first absorption wavelength emitted by a substance;
the first absorption wavelength being selected from the group consisting of a water absorption wavelength of 1.45 $\mu$m, and a cellulose absorption wavelength at one of 1.57 $\mu$m, 1.73 $\mu$m, and 2.1 $\mu$m;
means for monitoring the first absorption wavelength with a first near-infrared linear array;
means for blocking the first wavelength from reaching a second near-infrared linear array; and
means for characterizing data from the arrays into information on a property of the substance.

22. The system of claim 21 wherein the means for filtering includes:
means for filtering out a water absorption wavelength.

23. The system of claim 21 wherein the means for filtering includes:
means for filtering out a cellulose absorption wavelength.

24. The system of claim 21 further comprising:
means for filtering out a second absorption wavelength emitted by the substance;
means for monitoring the second absorption wavelength with a third near-infrared linear array; and
means for blocking the first and second wavelength from reaching the second near-infrared linear array.

25. The system of claim 24 wherein:
the first absorption wavelength is a water absorption wavelength; and
the second absorption wavelength is a cellulose absorption wavelength.

26. The system of claim 21 further comprising:
means for routing emissions from the substance to the arrays with a beam-splitter.

27. The system of claim 21 further comprising:
means for routing emissions from the substance to the arrays with a dichroic mirror.

28. The system of claim 21 further comprising:
means for routing emissions from the substance to the arrays with a prism.

* * * * *